(12) United States Patent
Schader et al.

(10) Patent No.: US 11,583,634 B2
(45) Date of Patent: Feb. 21, 2023

(54) PLUNGER AND DRUG DELIVERY DEVICE

(71) Applicant: SANOFI, Paris (FR)

(72) Inventors: Marc Schader, Frankfurt am Main (DE); Hugo Revellat, Cambridgeshire (GB); William Timmis, Cambridgeshire (GB)

(73) Assignee: Sanofi

( * ) Notice: Subject to any disclaimer, the term of this patent is extended or adjusted under 35 U.S.C. 154(b) by 48 days.

(21) Appl. No.: 16/758,676

(22) PCT Filed: Nov. 1, 2018

(86) PCT No.: PCT/EP2018/079916
§ 371 (c)(1),
(2) Date: Apr. 23, 2020

(87) PCT Pub. No.: WO2019/086562
PCT Pub. Date: May 9, 2019

(65) Prior Publication Data
US 2020/0345936 A1 Nov. 5, 2020

(30) Foreign Application Priority Data
Nov. 3, 2017 (EP) .................................... 17306519

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31511* (2013.01); *A61M 5/3204* (2013.01)

(58) Field of Classification Search
CPC ............ A61M 5/2033; A61M 5/31511; A61M 5/3204; A61M 2005/31598;
(Continued)

(56) References Cited

U.S. PATENT DOCUMENTS 3,473,646 A * 10/1969 Burke .................... A61M 5/002
206/229
3,702,609 A * 11/1972 Steiner .............. A61M 5/31591
604/139

(Continued)

FOREIGN PATENT DOCUMENTS

| CN | 101170925 | 4/2008 |
|---|---|---|
| CN | 201149919 | 11/2008 |

(Continued)

OTHER PUBLICATIONS

PCT International Preliminary Report on Patentability in International Application No. PCT/EP2018/079916, dated May 5, 2020, 7 pages.

(Continued)

*Primary Examiner* — Theodore J Stigell
*Assistant Examiner* — Nidah Hussain
(74) *Attorney, Agent, or Firm* — Fish & Richardson P.C.

(57) ABSTRACT

The present specification relates to a plunger configured to transmit a force from an energy source to a piston of a primary container, the plunger comprising a plunger rod configured to be subjected to the force from the energy source, the plunger rod having an inner surface forming a cavity, wherein a support element adapted to constrain the energy source within the cavity protrudes radially inwards from the inner surface into the cavity.

23 Claims, 4 Drawing Sheets

(58) Field of Classification Search
CPC ........... A61M 2005/2093; A61M 2005/14506; A61M 5/3125; A61M 5/31583; A61M 5/31585; A61M 5/1454; A61M 15/20; A61M 5/31525
USPC ......................................................... 604/135
See application file for complete search history.

(56) References Cited

U.S. PATENT DOCUMENTS

| | | | | |
|---|---|---|---|---|
| 5,324,265 | A | * | 6/1994 | Murray ............... A61M 5/3234 604/110 |
| 5,851,197 | A | | 12/1998 | Marano et al. |
| 7,841,794 | B2 | | 11/2010 | Salciarini et al. |
| 9,636,463 | B2 | | 5/2017 | Kakiuchi et al. |
| 2005/0027255 | A1 | | 2/2005 | Lavi et al. |
| 2009/0177156 | A1 | | 7/2009 | MacLean |
| 2010/0262125 | A1 | | 10/2010 | Matusch |
| 2011/0196313 | A1 | | 8/2011 | Mudd |
| 2013/0085457 | A1 | * | 4/2013 | Schiff ................... B65D 77/32 604/228 |
| 2014/0025006 | A1 | * | 1/2014 | Takemoto ........... A61M 5/2033 604/110 |
| 2015/0119799 | A1 | * | 4/2015 | Wotton ................ A61K 31/519 604/68 |

FOREIGN PATENT DOCUMENTS

| | | |
|---|---|---|
| CN | 201767532 | 3/2011 |
| CN | 102893203 | 1/2013 |
| CN | 102917738 | 2/2013 |
| CN | 103338798 | 10/2013 |
| CN | 103732276 | 4/2014 |
| CN | 105102043 | 11/2015 |
| CN | 105413023 | 3/2016 |
| CN | 105682707 | 6/2016 |
| CN | 105979989 | 9/2016 |
| CN | 106061529 | 10/2016 |
| CN | 106150328 | 11/2016 |
| CN | 206250687 | 6/2017 |
| CN | 206485082 | 9/2017 |
| JP | 2017-501752 | 1/2017 |
| WO | WO 1996/027083 | 9/1996 |
| WO | WO 2010/066590 | 6/2010 |
| WO | WO 2011/121554 | 10/2011 |
| WO | WO 2011/123024 | 10/2011 |
| WO | WO 2012/173554 | 12/2012 |
| WO | WO 2014/166926 | 10/2014 |
| WO | WO 2015/055588 | 4/2015 |
| WO | WO 2015/114158 | 8/2015 |
| WO | WO 2015/121080 | 8/2015 |
| WO | WO 2016/193375 | 12/2016 |
| WO | WO 2017/089289 | 6/2017 |

OTHER PUBLICATIONS

International Search Report and Written Opinion in Application No. PCT/EP2018/079916, dated Nov. 27, 2018, 11 pages.

* cited by examiner

PLUNGER AND DRUG DELIVERY DEVICE

CROSS REFERENCE TO RELATED APPLICATIONS

The present application is the national stage entry of International Patent Application No. PCT/EP2018/079916, filed on Nov. 1, 2018, and claims priority to Application No. EP 17306519.4, filed on Nov. 3, 2017, the disclosures of which are incorporated herein by reference.

TECHNICAL FIELD

The disclosure generally relates to a plunger for a drug delivery device and to a drug delivery device having such a plunger.

BACKGROUND

Many drug delivery devices comprise a drug cartridge having a piston for displacing a drug from the drug cartridge. The piston may be driven by a plunger which is subjected to a force of an energy source, e.g. a spring.

SUMMARY

It is an object of the present disclosure to provide an improved plunger for a drug delivery device and an improved drug delivery device having such a plunger.

The object is achieved by a plunger according to claim 1 and by a drug delivery device according to claim 11.

Exemplary embodiments are provided in the dependent claims.

In accordance with an aspect of the present disclosure, a plunger is configured to transmit a force from an energy source to a piston of a primary container, the plunger comprises a plunger rod configured to be subjected to the force from the energy source, the plunger rod having an inner surface forming a cavity wherein a support element adapted to constrain the energy source within the cavity protrudes radially inwards from the inner surface into the cavity.

In particular, the plunger rod has a longitudinal axis and an inner surface forming an elongated cavity along the longitudinal axis, wherein a support element adapted to constrain the energy source within the elongated cavity protrudes radially inwards from the inner surface into the elongated cavity to radially support the energy source within the elongated cavity. Furthermore, the plunger rod is configured as a one-piece plunger rod. According to a further disclosure, the support element is an inner integral part of the one-piece plunger rod.

Delivery of drugs, in particular drugs with higher viscosity through a narrow lumen of a needle, require relatively high forces on the piston. The energy source, e.g. a spring arranged on a plunger drives the piston, must thus provide a sufficiently high force to achieve a movement of the piston. When the delivery is started, the cartridge, e.g. a glass or plastic cartridge, or a finger flange of the cartridge may thus be subjected to high loads resulting in risk of breaking them. As the spring expands during injection, the spring buckles on the plunger, e.g. within a plunger rod, which leads to friction between plunger and spring. This causes an undesirable scratching sound during injection. The support element prevents the undesirable scratching sound during injection. Further, the support element avoids buckling out of e.g. coils of the extending spring into additional space available along the inner surface of the plunger rod.

In an exemplary embodiment, the support element is formed as an inner rib on the inner surface. In particular, the ribs are straight elements and rounded.

In another exemplary embodiment, a plurality of support elements is distributed around the inner surface of the cavity. In particular, the support elements are symmetrically or uniformly distributed around the inner surface of the cavity.

According to a further aspect, an edge at an open end of the cavity has a chamfer or a radius. Additionally, an inner diameter of the cavity increases in a region of the open end of the cavity in the direction to the open end.

In an exemplary embodiment, the support element is integrally formed with the plunger rod. In particular, the support element is formed on the plunger rod by one component moulding or two component moulding or three component moulding. Further, the support element is formed onto the inner surface of the inner elongated cavity of the plunger rod.

The disclosure further relates to a drug delivery device comprising a primary container or container defining a drug cavity for receiving a drug and having an outlet and a piston or a piston slidably arranged within the drug cavity, wherein the drug delivery device further comprises a plunger as described above and an energy source arranged to exert a force on the inner surface of the plunger rod.

In an exemplary embodiment, the energy source is a spring. Furthermore, the cartridge or container is prefilled with drug, in particular an emergency drug, e.g. an allergic drug or a diabetic drug, e.g. hypoglycemia, or biologics. The drug delivery device is for instance an auto-injector, a pen-injector or a syringe.

In a further embodiment, the piston or stopper slides inside the container to inject the drug. Additionally, the drug delivery device comprises actuator means for automatically injecting a patient with said drug.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
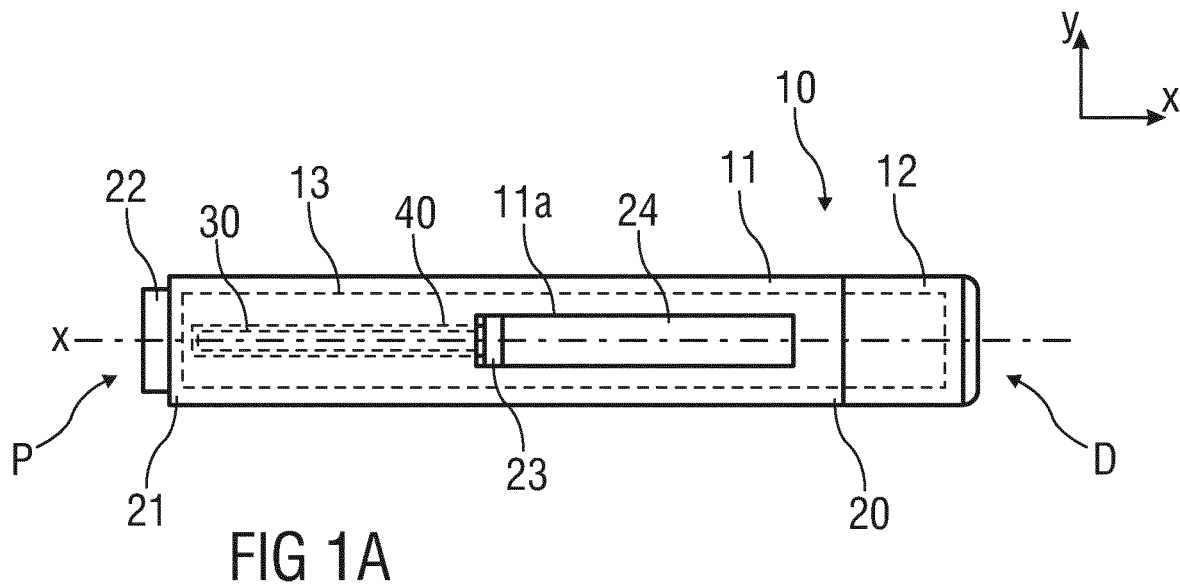
FIGS. 1A to 1B are schematic views of drug delivery devices.
Figure 1B:
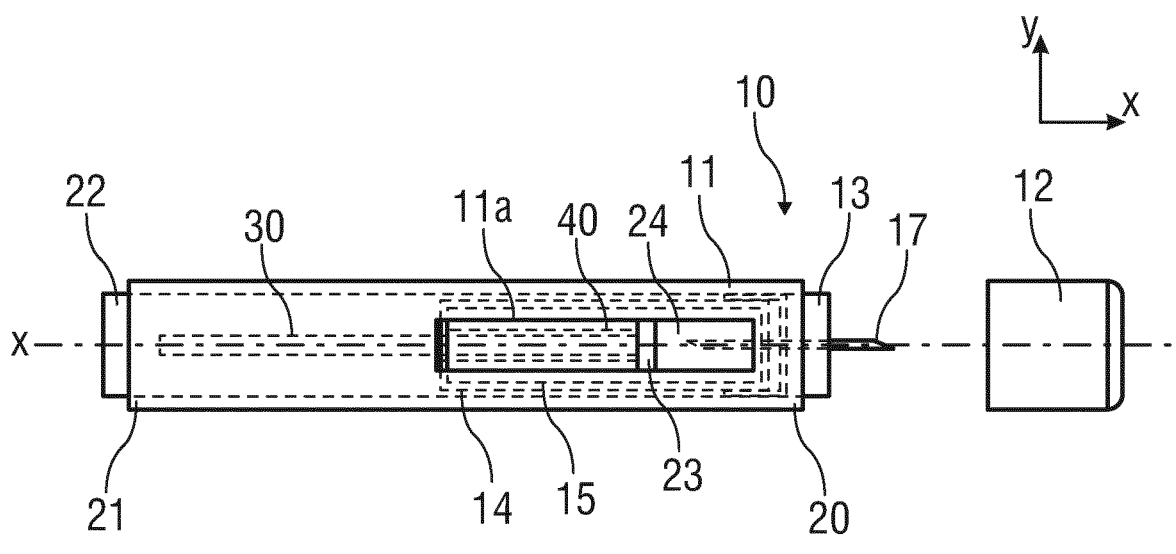

According to some embodiments of the present disclosure, an exemplary drug delivery device 10 is shown in FIGS. 1A and 1B.

Device 10, as described above, is configured to inject a drug or medicament into a patient's body.

Device 10 includes a housing 11 which typically contains a reservoir containing the medicament to be injected (e.g., a syringe 24 or a container) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal region 20 of housing 11. Insertion of the needle 17 can occur via several mechanisms. For example, the needle 17 may be fixedly located relative to housing 11 and initially be located within an extended needle sleeve 13. Proximal movement of the sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to housing 11. Such insertion can be triggered by movement of sleeve 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a sleeve trigger mechanism, e.g. provided by pushing the needle sleeve 13 inside the housing when the drug delivery device is put onto an injection side.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, an energy source, e.g. a drive spring 30 is arranged in a plunger 40 and is under compression before device 10 is activated. A proximal end of the drive spring 30 can be fixed within proximal region 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11a through which the syringe 24 can be monitored.

Figure 2:
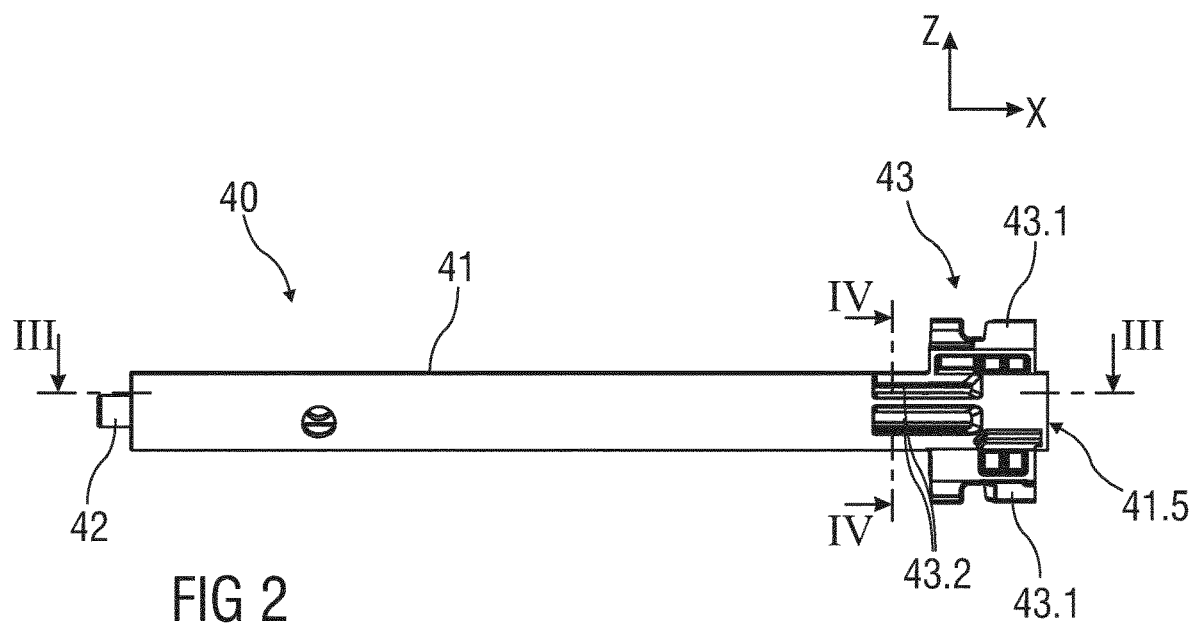
FIG. 2 is a schematic view of an embodiment of a plunger for a drug delivery device.

FIG. 2 is a schematic view of an exemplary embodiment of the plunger 40 for the drug delivery device 10.

The plunger 40 is configured to transmit a force from the spring 30 as an energy source to the piston 23 of the drug syringe 24. The plunger 40 comprises a plunger rod 41. The plunger rod 41 comprises at its distal end a connecting element 42. The connecting element 42, e.g. a pin, for instance a threadable pin, is adapted to couple with the piston 23 in a force-fit and/or friction-fit manner. The plunger 40 is formed as a one-piece plunger.

On its proximal end the plunger rod 41 comprises coupling elements 43, e.g. projections 43.1 and/or openings 43.2, to releasably couple plunger rod 41 with needle sleeve 13 and/or housing 11 for activating drug delivery device 10.

The plunger rod 41 further has in general a form of a hollow cylinder. At the distal end, the plunger rod 41 is closed. On the opposite proximal end, the plunger rod 41 is open and has an open end 41.5.

Figure 3:
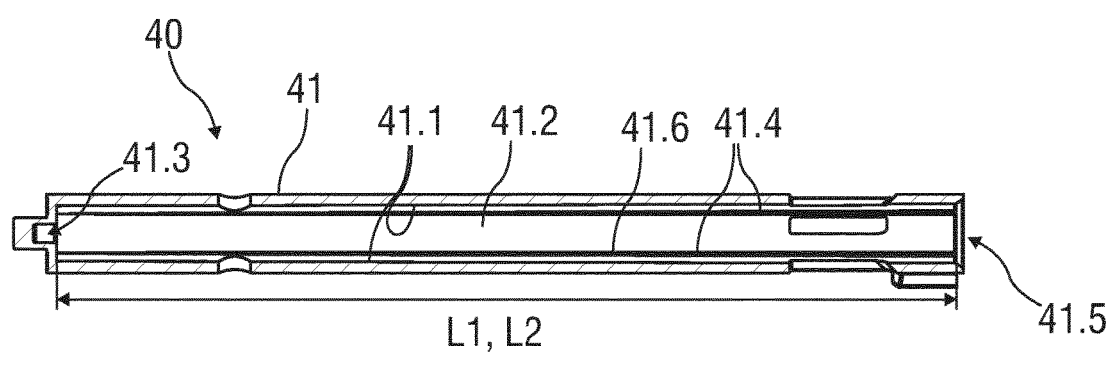
FIG. 3 is a view of a longitudinal section of a plunger.

FIG. 3 is a view of a longitudinal section of plunger 40. The plunger rod 41 has an inner surface 41.1 forming a cavity 41.2 configured to be subjected to a force from an energy source, e.g. drive spring 30. The drive spring 30 is shown in FIGS. 1A, 1B.

The drive spring 30 is arranged to exert a force on a proximally facing surface 41.3 of the plunger rod 41. In the illustrated embodiment, the drive spring 30 is a compression spring arranged within the hollow plunger rod 41, e.g. within the cavity 41.2, and acting on the proximally facing surface 41.3 arranged within the plunger rod 41.

In alternative embodiments, the proximally facing surface 41.3 may be arranged at a proximal end or at another location along a surface of the plunger rod 41. The drive spring 30 may be proximally grounded in the housing 11 (as shown in FIGS. 1A, 1B) in which the drug cartridge or syringe or primary container 24 is retained. A trigger mechanism, e.g. button 22 (shown in FIGS. 1A, 1B) may be arranged to operatively prevent or allow movement of the plunger rod 41.

The inner surface 41.1 further comprises a support element 41.4 adapted to constrain the spring 30 within the plunger 40, in particular within the cavity 41.2 of the plunger rod 41. In particular, the support element 41.4 is configured to press against the spring 30. The support element 41.4 allows to securely hold the spring 30 in place within the plunger cavity 41.2 and to prevent rattle noises due to spring movement during injection. Further, buckling out of coils of the spring 30 into additional space within the plunger rod 41 is also prevented.

The support element 41.4 radially protrudes from the inner surface 41.1 inwards into the cavity 41.2. Furthermore, the support element 41.4 has a length L1 which corresponds with the length L2 of the cavity 41.2. Alternatively, the support element 41.4 has a length which is shorter than the length of the cavity 41.2. In this case, the support element 41.4 is arranged at least in the region of the open end 41.5 of the plunger rod 41 and extends inwards into the cavity 41.2.

In an exemplary embodiment, the support element 41.4 is formed as an inner rib 41.6 on the inner surface 41.1. In particular, the ribs 41.4 are straight elements and rounded. In particular, the top of the ribs 41.4 are rounded.

Figure 4:
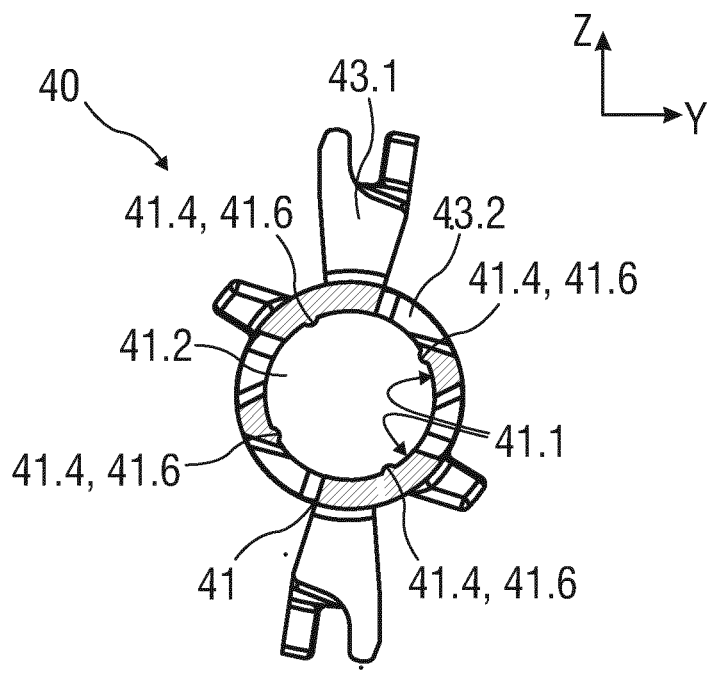
FIG. 4 is a view of a cross section of a plunger.

FIG. 4 is a view of a cross section of plunger 40. As best seen, a plurality of support elements 41.4 is distributed around the inner surface 41.1 of the cavity 41.2. In particular, the support elements 41.4 are symmetrically distributed around the inner surface 41.1. Due to the symmetric arrangement of the support elements 41.4 misalignment of the spring 30 arranged within the cavity 41.2 is reduced which leads to a rattle-free arrangement of the spring 30 inside the plunger rod 41. Further, due to the press- or friction-fit coupling of the spring 30 within the cavity 41.2 by the symmetrically arranged support elements 41.4, the spring 30 operates smoothly and without noise generation during injection.

Figure 5:
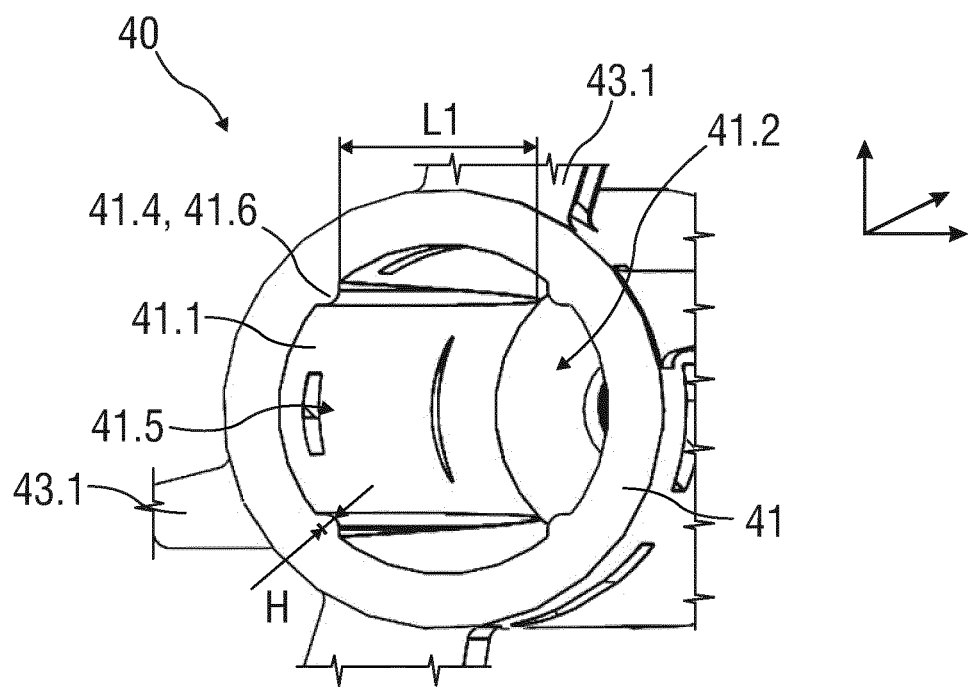
FIG. 5 is an enlarged perspective view of a cross section of a plunger.

FIG. 5 shows an enlarged perspective view of a cross section of plunger 40 with shortened and rounded support elements 41.4 symmetrically distributed around the inner surface 41.1 of the cavity 41.2.

A length L1 of the shortened support elements 41.4 is shorter than the length L2 of the cavity 41.2. Further, a height H of the support elements 40 decreases from the open end 41.5 of the plunger rod 41 inwards into the cavity 41.2. This results in an initial clamping contact of the spring 30 within the cavity 41.2 in the region of the open end 41.5, e.g. at the beginning of the injection when the spring 30 comes into contact with the inner surface 41.1 of the plunger 40.

Alternatively, the height H of the support elements 41.4 increases from the open end 41.5 inwards into the cavity 41.2. This ensures that the spring 30 is securely held inside the plunger rod 41 during the whole injection process and the whole movement of the drive spring 30.

Figure 6:
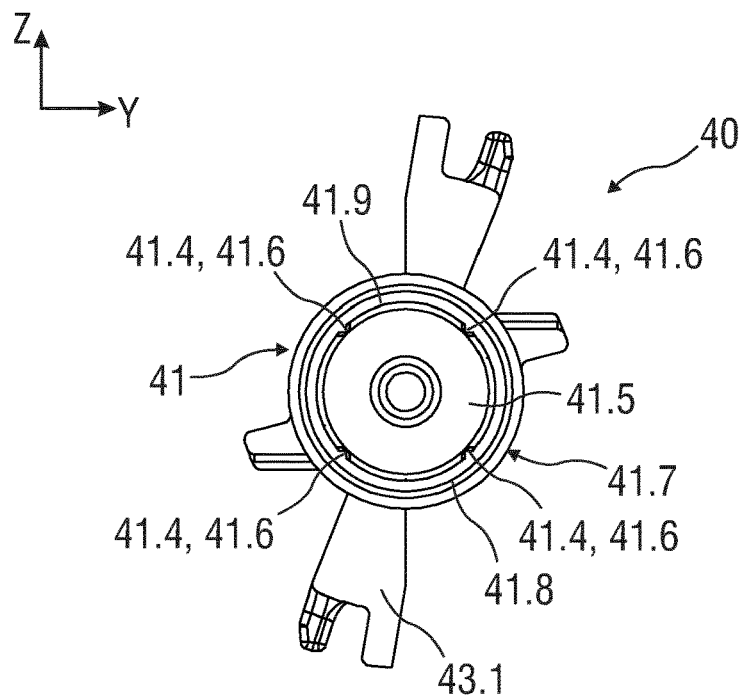
FIG. 6 is a top view of an open end of a plunger.
Figure 7:
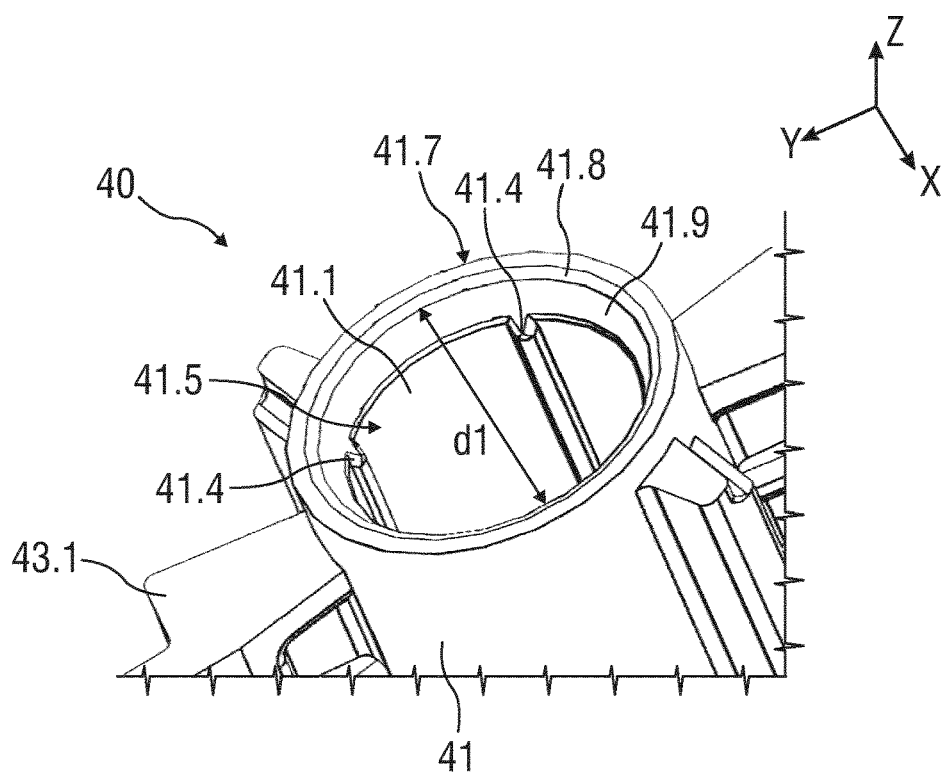
FIG. 7 is an enlarged perspective top view of a plunger.

FIG. 6 is a top view of the open end 41.5 of the plunger 40 and FIG. 7 is an enlarged perspective view onto a top view of plunger 40.

The plunger rod 41 further comprises an edge 41.7 at the open end 41.5 of the cavity 41.2. The edge 41.7 has a chamfer 41.8. The chamfer 41.8 serves to remove sharp edges at the open end 41.5 and allows that the drive spring 30 can catch as it expands.

The plunger rod 41 is further configured such that an inner diameter d1 of the cavity 41.2 increases in a region 41.9 of the open end 41.5. Such in particular gradual increasing of the inner diameter d1 at the open end 41.5 of the plunger 40 removes a sudden transition which allows the spring 30 to rapidly and smoothly introduce into free space and, thus, into the plunger rod 41.

The support element/s 41.4 described above may be integrally formed with the plunger rod 41. In particular, the support element/s 41.4 may be formed on the plunger rod 41 by two component moulding or three component moulding.

According to the disclosure mentioned above, the internal or inner support element/s 41.4 within the plunger core or cavity 41.2 reduces clearance to the spring 30 and prevents the spring 30 from buckling as it expands during injection. In addition the rear or proximal edge 41.7 of the plunger 40 is sloped to remove sharp edges so that the spring 30 can be better catch on and can be smoother moved within the plunger rod 41.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 10 drug delivery device
11 housing
11a window
12 cap assembly
12.1 needle shield
12.2 cap
13 needle sleeve
17 needle
20 distal region of the drug delivery device
21 proximal region of the drug delivery device
22 button
23 piston
24 syringe or container or cartridge
30 energy source, e.g. drive spring
40 plunger
41 plunger rod
41.1 inner surface
41.2 cavity
41.3 proximal facing surface
41.4 support element
41.5 open end
41.6 rib
41.7 edge
41.8 chamfer
41.9 region
42 connecting element
43 coupling element
43.1 projection
43.2 opening
D distal or front end
d1 diameter
L1, L2 length
P proximal or back end
X longitudinal axis

The invention claimed is:

1. A plunger configured to transmit a force from an energy source to a piston of a primary container, the plunger comprising:
   a plunger rod configured to be subjected to the force from the energy source, the plunger rod having a longitudinal axis and an inner surface forming an elongated cavity along the longitudinal axis; and
   a support element adapted to constrain the energy source within the elongated cavity and protruding radially inwards from the inner surface into the elongated cavity to radially support the energy source within the elongated cavity.

2. The plunger according to claim 1, wherein the support element has a first length that corresponds to a second length of the cavity.

3. The plunger according to claim 1, wherein the support element is formed as an inner rib on the inner surface.

4. The plunger according to claim 3, wherein the inner rib is a straight element and is rounded.

5. The plunger according to claim 1, further comprising additional support elements, wherein the support element and the additional support elements together provide a plurality of support elements that are distributed around the inner surface of the cavity.

6. The plunger according to claim 5, wherein the plurality of support elements is symmetrically distributed around the inner surface of the cavity.

7. The plunger according to claim 1, wherein an edge at an open end of the cavity has a chamfer.

8. The plunger according to claim 7, wherein an inner diameter of the cavity increases in a region of the open end of the cavity.

9. The plunger according to claim 1, wherein the support element is integrally formed with the plunger rod.

10. The plunger according to claim 1, wherein the support element is formed on the plunger rod by two component mouldings or three component mouldings.

11. The plunger according to claim 1, wherein the elongated cavity is contained within an interior region of the plunger rod.

12. The plunger according to claim 1, wherein the inner surface of the plunger rod is an interior surface.

13. The plunger according to claim 1, wherein the support element is arranged to contact a radially facing surface of the energy source to radially support the energy source.

14. A drug delivery device, comprising:
   a primary container defining a drug cavity for receiving a drug and having an outlet and a piston slidably arranged within the primary container; and
   a plunger configured to transmit a force to the piston of the primary container, the plunger comprising:
      a plunger rod having a longitudinal axis and an inner surface forming an elongated cavity along the longitudinal axis,
      an energy source arranged within the elongated cavity of the plunger rod to exert a force on the inner surface of the plunger rod, and
      a support element adapted to constrain the energy source within the elongated cavity and protruding radially inwards from the inner surface into the elongated cavity to radially support the energy source within the elongated cavity.

15. The drug delivery device according to claim 14, wherein the energy source comprises a spring.

16. The drug delivery device according to claim 14, wherein the primary container is prefilled with a drug.

17. The drug delivery device according to claim 14, wherein the drug delivery device is an auto-injector, a pen-injector, or a syringe.

18. The drug delivery device according to claim 14, wherein the support element has a first length that corresponds to a second length of the cavity.

19. The drug delivery device according to claim 14, wherein the support element is formed as an inner rib on the inner surface.

20. The drug delivery device according to claim 19, wherein the inner rib is a straight element and is rounded.

21. The drug delivery device according to claim 14, wherein the plunger further comprises additional support elements, and wherein the support element and the additional support elements together provide a plurality of support elements that are distributed around the inner surface of the cavity.

22. The drug delivery device according to claim 14, wherein an edge at an open end of the cavity has a chamfer, and wherein an inner diameter of the cavity increases in a region of the open end of the cavity.

23. The drug delivery device according to claim 14, wherein the support element is integrally formed with the plunger rod.

* * * * *

UNITED STATES PATENT AND TRADEMARK OFFICE
CERTIFICATE OF CORRECTION

| | |
|---|---|
| PATENT NO. | : 11,583,634 B2 |
| APPLICATION NO. | : 16/758676 |
| DATED | : February 21, 2023 |
| INVENTOR(S) | : Marc Schader, Hugo Revellat and William Timmis |

It is certified that error appears in the above-identified patent and that said Letters Patent is hereby corrected as shown below:

On the Title Page

Column 1 (Item (73), Assignee), Line 1, delete "Sanofi" and insert -- Sanofi, Paris (FR) --

Signed and Sealed this
Ninth Day of May, 2023

Katherine Kelly Vidal
*Director of the United States Patent and Trademark Office*